US00PP08373P

United States Patent [19]

Snow

[11] Patent Number: Plant 8,373

[45] Date of Patent: Sep. 14, 1993

[54] BEGONIA PLANT NAMED SCENTIMENT YELLOW

[75] Inventor: Andrew B. Snow, Watsonville, Calif.

[73] Assignee: Golden State Bulb Growers, Watsonville, Calif.

[21] Appl. No.: 888,335

[22] Filed: May 22, 1992

[51] Int. Cl.[5] ..... A01H 5/00

[52] U.S. Cl. ..... Plt./87.18

[58] Field of Search ..... Plt./87.18

[56] References Cited

U.S. PATENT DOCUMENTS

P.P. 7,569 6/1991 Siebold ..... Plt. 87.18

*Primary Examiner*—James R. Feyrer

*Attorney, Agent, or Firm*—Foley & Lardner

[57] ABSTRACT

A distinct cultivar of begonia plant named Scentiment Yellow, characterized by its fully double and symmetrical male flowers and single female flowers, rich solid yellow main flower color, distinct fragrance, and its plant habit full and pendulous with numerous flowering shoots.

1 Drawing Sheet

1

The present invention relates to a new and distinctive cultivar of begonia plant, botanically known as begonia *Tuberhybrida pendula,* and known by the cultivar name Scentiment Yellow.

The new cultivar was discovered by the inventor Andrew B. Snow as a mutation of the begonia cultivar named Golden Anniversary, disclosed in U.S. Plant Pat. No. 7,569. The mutation was observed in a group of 15,000 field-planted cloned plants of the parent cultivar under cultivated growth at Watsonville, Calif.

Subsequent asexual reproduction by leaf cuttings by the inventor has established that the unique features of the new cultivar are produced through successive propagations at the above noted location.

The following characteristics distinguish the new begonia from both its parent and other begonias commercially known and used in the floriculture industry:

1. The flowers have a definite and distinct fragrance that can be described as gently sweet but not overpowering. It is often compared to the scent of a fragrant rose bloom. The fragrance is most pronounced when the temperature is between 70° and 80° F.

2. The male flowers are fully double and symmetrical, and do not produce pollen or visible male reproductive parts under normal growing conditions. Female flowers are single.

3. The flower color is a rich solid yellow, with the back of the exterior petals being tinged with red, especially when grown under high light.

4. The plant habit is full and pendulous with numerous flowering shoots (5–6 or more). Each flowering shoot will produce anywhere from 4–5 peduncles with 1 or 2 male flowers on each during the course of a growing season.

There are no begonia cultivars with which the new cultivar can be meaningfully compared. The brilliant yellow flower color, the full symmetrical double male flowers and the distinct fragrance combine to describe a unique begonia.

The accompanying colored photographs taken Sep. 20, 1991 illustrate the overall appearances of the new cultivar when grown in a 10" plastic pot. The top photograph is a side view of a mature flowering plant of Scentiment Yellow. The bottom photograph comprises an enlarged showing of the top sides and underside of typical male and female flowers. The colors illustrated

2 are as true as it is reasonably possible to obtain in colored reproductions of this type.

The following is a detailed description of my new begonia cultivar based on plants produced under commercial practices in Watsonville, Calif. Color references are made to the Royal Horticultural Society Colour Chart except where general terms of ordinary dictionary significance are used.

Parentage: Mutation of begonia cultivar Golden Anniversary.

Propagation:

A. *Type cutting.*—Leaf cuttings.

B. *Time to root.*—24–30 days at 21° C. summer; 32–38 days at 21° C. winter.

C. *Rooting habit.*—Abundant, fibrous, dendritic.

D. *Time for shoot development.*—Slow; 10–14 weeks in summer and up to 16 weeks in winter. Shoot count is medium to high in summer and less in winter.

Plant description:

A. *Form.*—Low, mounding, pendulous; herbaceous.

B. *Habit of growth.*—Slow, uniform with numerous shoots and good branching habit. At full growth the plant is well rounded and approximately 18–24 inches both in height and width, with pendulous flowering shoots.

C. *Foliage.*—Simple, alternate, and borne on semi-rigid 6–8 inch petioles. 1. Size: At maturity, the leaves reach 10–12 inches from base to apex, and at their widest point the leaves are up to 7" across. 2. Shape: Broad-ovate, obliquely cordate, broadly acuminate with rounded basal lobes. 3. Texture: Firm, crisp, but not brittle; hirtellous on both surfaces with a ciliate tendency on bottom surface. 4. Margin: Doubly serrate. 5. Color: Young foliage, top side: slightly darker than 143A; under side: 147C. Mature foliage, top side 146A and B; under side: 147C. 6. Venation: Reticulate.

Flowering description:

A. *Flowering habits.*—Flowering is presented on a semi-pendulous raceme. Often, but not always, secondary male and female flowers will develop below the primary flowers. Some peduncles will have a solitary male flower with a solitary female flower, while others may have two matching female flowers per male.

B. *Natural flowering season.*—Natural flowering occurs in the summer and fall months.

C. *Flower buds.*—Flat, nearly round, tending toward bell shaped.

D. *Flowers borne.*—On small pedicels originating from long ($7\frac{1}{2}''$ to $8\frac{1}{2}''$) axillary peduncles, resulting in one male flower with one or two female flowers, and occasionally a secondary male and female flower as raceme develops.

E. *Quantity.*—Flowering ranges from 2–5 flowers per peduncle and numerous (3–5) peduncles per shoot, with 4–6 shoots per plant.

F. *Tepals.*—1. Shape: Oval to tear drop shaped. 2. Color: Top side in spring/summer when opening is yellow 14C with orange 14B at the center; underside is orange 27C at the center fading to almost white at the edge. The outermost petals are tinged light rose 49C on the back, especially when grown in high light. 3. Number of tepals: 45–46 on male flowers, 5 on female flowers. 4. Size of tepals: Outer (male), up to $2\frac{3}{4}'' \times 2\frac{3}{4}''$, inner $\frac{3}{8}'' \times \frac{3}{8}''$; $1\frac{1}{2}'' \times 1\frac{3}{4}''$ to $1\frac{5}{8}'' \times 2''$ (female). 5. Flower size: Male, $5'' \times 5''$; female, $4'' \times 4''$.

G. *Reproductive organs.*—1. Stamens: None. 2. Pistils: a. Stigma: Shape, multi-lobed, color 15A. b. Style color: 15A. C. Ovaries: Three in number, syncarpous; $\frac{3}{8}''$ to $\frac{5}{8}''$ in total size; pale green (142C) in color with sheen on exterior.

Disease resistance: Scentiment Yellow has shown excellent disease resistance to date.

I claim:

1. A new and distinct cultivar of begonia plant named Scentiment Yellow, as illustrated and described.

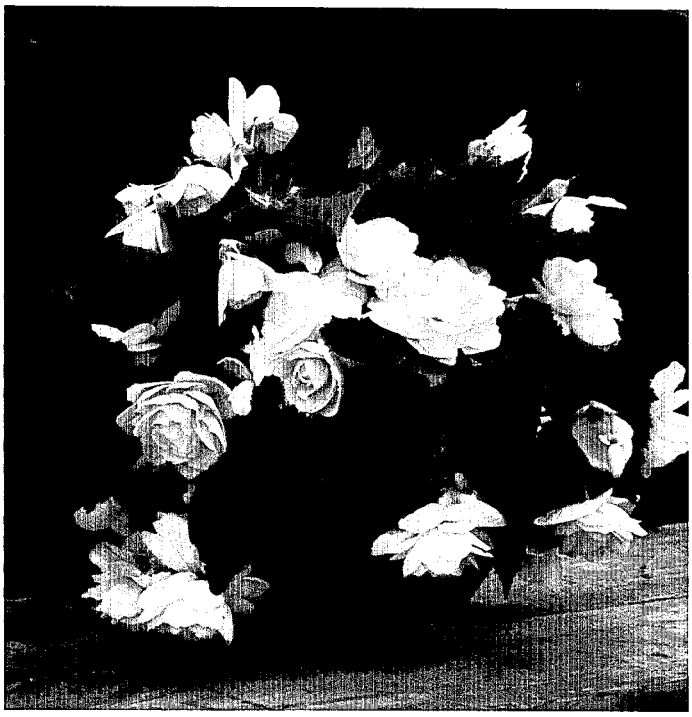
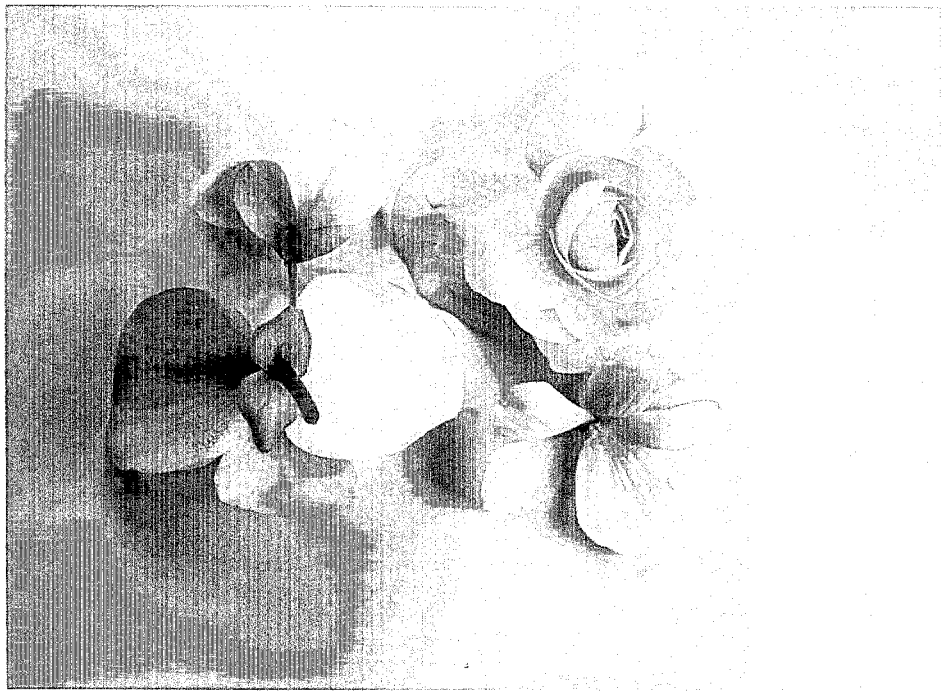

* * * * *